United States Patent [19]

Mullen

[11] Patent Number: 5,160,418
[45] Date of Patent: Nov. 3, 1992

[54] ENZYME ELECTRODES AND IMPROVEMENTS IN THE MANUFACTURE THEREOF

[75] Inventor: William H. Mullen, Ely, Great Britain

[73] Assignee: Cambridge Life Sciences plc, Ely, England

[21] Appl. No.: 381,580

[22] Filed: Jul. 18, 1989

[30] Foreign Application Priority Data

Jul. 28, 1988 [GB] United Kingdom ............... 8817997

[51] Int. Cl.⁵ .................... G01N 27/26; C25F 7/00
[52] U.S. Cl. ................... 204/153.12; 204/403; 204/418; 435/817
[58] Field of Search ............ 204/403, 418, 153.12, 204/153.2, 290 R, 291, 294; 435/817, 179

[56] References Cited

U.S. PATENT DOCUMENTS

| | | | |
|---|---|---|---|
| 4,044,193 | 8/1977 | Petrow et al. | 429/40 |
| 4,166,143 | 8/1979 | Petrow et al. | 427/115 |
| 4,229,490 | 10/1980 | Frank et al. | 427/115 |
| 4,293,396 | 10/1981 | Allen et al. | 204/106 |
| 4,392,933 | 7/1983 | Nakamura et al. | 204/403 |
| 4,478,696 | 10/1984 | Allen | 204/106 |

FOREIGN PATENT DOCUMENTS

56-163447 12/1981 Japan.
87/07295 12/1987 PCT Int'l Appl..
89/03871 5/1989 PCT Int'l Appl..

OTHER PUBLICATIONS

Differential Pulse Voltammetric Study of Direct Electron Transfer in Glucose Oxidase Chemically Modified Graphit Electrodes, 54 Anal. Chem 1982, 1098–1101.
A Chemically-Modified Enzyme Membrane Electrode as an Amperometric Glucose Sensor, T. Yao, 148 Analytica Chimica Acta 1983, 27–33.
Enzyme Electrode for the Determination of Glucose, 53 Anal. Chem. 1981, 51–53.

*Primary Examiner*—John Niebling
*Assistant Examiner*—Bruce F. Bell
*Attorney, Agent, or Firm*—St. Onge Steward Johnston & Reens

[57] ABSTRACT

Enzyme electrodes are disclosed consisting essentially of a uniform homogeneous layer of a finely divided platinum group metal or oxide, preferably preadsorbed onto the surface of an activated carbon or grapite powder, and deposited from suspension upon the surface of an electrically conductive substrate and in admixture with an enzyme and optionally a water soluble or water-dispersible binder. Preferably the enzyme electrodes are produced by coating the substrate with a suspension of the enzyme, the finely divided platinum group metal, and if present the carbon or graphite powder and binder, and drying at a temperature below that at which the enzyme is deactivated.

45 Claims, 6 Drawing Sheets

ENZYME ELECTRODES AND IMPROVEMENTS IN THE MANUFACTURE THEREOF

FIELD OF INVENTION

This invention relates to enzyme electrodes and improvements in the manufacture thereof.

BACKGROUND AND PRIOR ART

In International Patent Application No. PCT/GB87/00365 (International Publication No. WO 87/07295) enzyme electrodes capable of responding amperometrically to the catalytic activity of the enzyme in the presence of its respective substrate are described comprising an enzyme immobilised or adsorbed onto the surface of an electrically conductive support member which consists of or comprises a porous layer of resin-bonded carbon or graphite particles, said particles having intimately mixed therewith, or deposited or adsorbed onto the surface of the individual particles prior to bonding to form said layer, a finely divided platinum group metal, thereby to form a porous, substrate layer onto which said enzyme is adsorbed or immobilised and comprising a substantially homogeneous layer of resin-bonded carbon or graphite particles, with said platinum group metal dispersed substantially uniformly throughout said layer. The preferred substrate materials are resin bonded platinised carbon paper electrodes comprising platinised carbon powder particles having colloidal platinum adsorbed on the surface of the particles and bonded onto a carbon paper substrate using a synthetic resin, preferably polytetrafluoroethylene, as the binder. The preferred enzyme electrodes are glucose oxidase electrodes comprising glucose oxidase adsorbed or immobilised onto the surface of the substrate.

In International Application No. PCT/GB88/00868 (International Publication No. WO 89/03871) similar enzyme electrodes are disclosed but using the oxides, e.g. PtO, rather than an elemental platinum group metal preadsorbed onto the resin-bonded carbon or graphite particles.

As described therein, the preferred substrate materials for those enzyme electrodes are resin bonded, platinised (or platinum oxide containing) carbon materials used hitherto as gas diffusion electrodes in fuel cells and available commercially from The Prototech Company, Newton Highlands, United States of America. Essentially such materials contain as the resin binder a relatively high melting point hydrophobic fluorocarbon resin, preferably polytetrafluoroethylene.

The manufacture of such resin-bonded platinised carbon, gas diffusion electrode materials is described in U.S. Pat. Nos. 4,044,193; 4,166,143; 4,293,396 and 4,478,696. Alternative, but similar gas diffusion electrode materials, equally suitable in accordance with the teachings of International Patent Publication WO 87/07295 as the electrically conductive substrate materials for enzyme electrodes are also disclosed in U.S. Pat. No. 4,229,490. Broadly speaking, such electrode materials are manufactured by depositing colloidal size particles of platinum or palladium, or other platinum group metal, onto finely divided particles of carbon or graphite, blending the platinised or palladised carbon or graphite particles with a fluorocarbon resin, preferably polytetrafluoroethylene, and moulding the mixture onto an electrically conductive support, preferably an electrically conductive carbon paper, or onto a filamentous carbon fibre web. Similar procedures apply to the oxide containing materials.

For use as an enzyme electrode in accordance with the teachings of International Publications WO 87/07295 and WO 89/03871, the appropriate enzyme, e.g. glucose oxidase, or mixture of enzymes, is immobilised or adsorbed onto the surface of a preformed web comprising a porous surface layer of resin-bonded platinised or palladised (those terms hereinafter being used in a generic sense to include the corresponding oxides as well as the elemental platinum group metals, unless the context requires otherwise) carbon or graphite particles, as described above. As indicated, the immobilised enzyme may simply be adsorbed onto the surface of the porous layer of resin-bonded, platinised or palladised carbon particles, or it may be covalently coupled thereto, for example, using well established enzyme immobilisation techniques, such as, for example, covalent bonding with a carbodiimide or carbonyldiimidazole reagent, covalent bonding with 1,6-dinitro-3,4-difluorobenzene, or by cross-linking with glutaraldehyde. In all cases, the enzyme or enzyme mixture is immobilised or adsorbed onto a preformed electrically conductive substrate comprising a porous layer of resin bonded platinised or palladised carbon or graphite particles moulded onto an electrically conductive substrate by the application of heat and pressure. In place of the finely divided platinum group metal, the corresponding oxides may be used, e.g. platinum or palladium oxide.

Amongst other relevant background prior art to be acknowledged herein are:

Ianiello et al (1982) Analyt. Chem. 54, 1098–1101 which describes mediatorless sensors in which glucose oxidase and L-amino acid oxidase are covalently bonded to a graphite electrode by the cyanuric chloride method;

Matsushita Electric Appliance Industry Company, Unexamined Japanese Patent Publication No. 56-16447 which discloses an enzyme electrode comprising an electrically conductive base of moulded graphite containing up to 10 parts by weight of a fluorocarbon resin binder, e.g. polytetrafluoroethylene, as the binder, and onto which is deposited by vapour phase deposition or electrolytically, a thin (less than 1 $\mu$m) film of platinum. The enzyme, e.g. glucose oxidase is immobilised onto the platinised surface of the electrically conductive base, the invention allegedly overcoming the problems of immobilising an enzyme directly onto platinum; and Matsushita Electrical Industrial Co. Ltd. (Nakamura et al) U.S. Pat. No. 4,392,933 in which is disclosed an immobilised enzyme electrode comprising an oxidoreductase enzyme, e.g. glucose oxidase, and a metal oxide, e.g. ruthenium oxide, capable of entering into the redox reaction coupled to the enzyme, the enzyme and the metal oxide, the metal oxide itself either itself forming an electron collector and conductor, or being incorporated into an electron collector and conductor material, such as graphite. When using graphite as the electron collector and conductor, the reactive metal oxide, e.g. $RuO_2$ in powder form and graphite powder are press moulded into a powder compact or disc, and onto which the enzyme, e.g. glucose oxidase, is immobilised by cross-linking to the graphite surface, for example, with glutaraldehyde.

OBJECT OF THE INVENTION

The above methods of producing an enzyme electrode are all essentially two stage methods, and require premoulding of the graphite or carbon base often under conditions requiring sintering of the moulded compact to fuse the binder, which, as indicated, has hitherto been a high melting point hydrophobic synthetic resin, preferably a fluorocarbon resin such as polytetrafluoroethylene.

Such methods, however, do not lend themselves to high volume, mass production techniques, as a result of which such prior art enzyme electrodes tend to be expensive. It would therefore be desirable to produce such electrodes by a simple, preferably one-step, mass production technique, which would lead to lower manufacturing costs, even to the extent of being able to produce one-off disposable enzyme electrodes, i.e. which can be used once only and then discarded. Such one-off disposable enzyme electrodes would be in great demand for a variety of medical tests and diagnoses.

SUMMARY OF INVENTION

In accordance with the present invention, it has been discovered that, in the manufacture of enzyme electrodes comprising an enzyme or mixture of enzymes immobilised or adsorbed onto a porous layer of resin-bonded platinised or palladised (or other platinum group metal) carbon or graphite particles, the high temperature binder (i.e. the high melting point fluorocarbon or other hydrophobic resin, preferably polytetrafluoroethylene) can either be dispensed with entirely, or replaced by a low temperature, preferably water-soluble or water-dispersible, binder such as gelatin, i.e. a binder which can be activated at room temperature, and which does not require high temperature sintering.

This greatly facilitates manufacture of the enzyme electrode since it is now possible to premix the enzyme or mixture of enzymes, with the platinised or palladised (or other platinum group metal containing) carbon or graphite particles in a liquid suspension medium, for example in water, and optionally containing the binder, thereby to form a suspension of enzyme, platinised or palladised finely divided carbon or graphite, and, optionally, a binder, and then to deposit that suspension, for example by a screen printing technique, as a thin film on the surface of an electrically conductive substrate, and thereafter drying the coated substrate thereby to deposit thereon a thin film comprising a substantially homogeneous blend of enzyme, platinised or palladised finely divided carbon or graphite, and, if present, the binder. The screen printing technique, in particular, enables the high volume production of a highly effective and highly sensitive enzyme electrode material.

Not only that, but it has also been discovered that, whilst the presence of finely divided carbon or graphite is preferred to act as an electron collector and conductor, it can, in fact, be dispensed with, and that functional enzyme electrodes can be obtained quite simply by depositing a suspension of finely divided platinum group metal, or a corresponding oxide, enzyme and optionally a low-temperature, preferably water soluble binder, on an electrically conductive track, e.g. a carbon track, or other suitable electrically conductive substrate, such as a sheet of electrically conductive carbon paper, and drying to deposit thereon a uniform layer comprising the finely divided platinum group metal or oxide, the enzyme and, if used, the binder as a substantially homogeneous dispersion.

DETAILED DESCRIPTION

Figure 1:
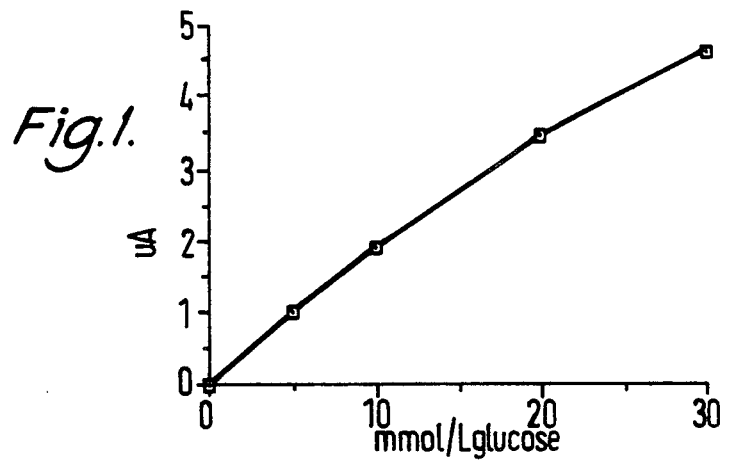
FIG. 1 shows the current output (uA) from the electrode of Example 1 to various concentrations of glucose[of Example 1].
Figure 2:
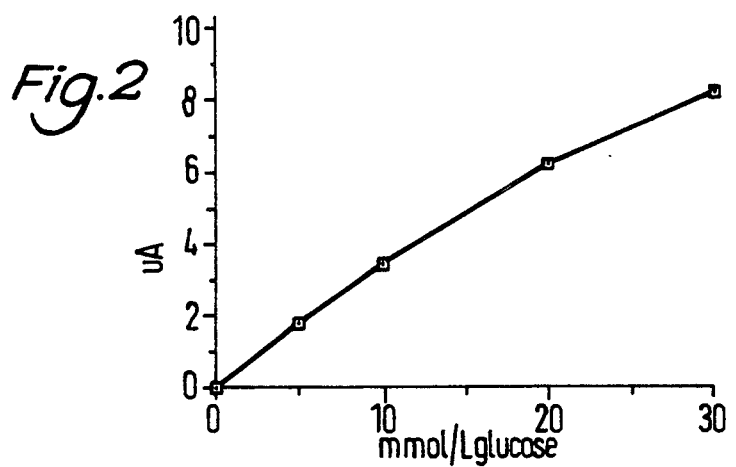
FIG. 2 shows the current output (uA) from the electrode of Example 2 to various concentrations of glucose[of Example 2].

In accordance with a first aspect of the present invention, therefore, there is provided a method for the manufacture of enzyme electrodes comprising a substantially homogeneous mixture of a finely divided platinum group metal or oxide and one or more enzymes deposited as an electrically conductive layer upon the surface of an underlying support, the electrode being amperometrically responsive to the activity of the enzyme when the enzyme containing a layer of the electrode is in contact with the respective enzyme substrate, the method comprising forming a substantially uniform suspension comprising the finely divided platinum group metal or oxide and said enzyme(s) suspended in a liquid suspension medium, depositing that suspension on the surface of the support member, and drying the deposited suspension at a temperature below the deactivation temperature of the enzyme thereby to deposit the finely divided platinum group metal or oxide and said enzyme(s) as a substantially uniform, homogeneous coating layer on the surface of the support.

In accordance with a second aspect, there is provided an enzyme electrode comprising a substantially homogeneous mixture of a finely divided platinum group metal or oxide and one or more enzymes deposited as an electrically conductive surface layer on the surface of an underlying support member, said layer also containing a binder for the particles of finely divided platinum group metal or oxide and said enzyme(s), wherein said binder comprises a material effective to bind the finely divided platinum group metal or oxide particles and said enzyme(s) into a coherent, cohesive layer bonded to the support at a temperature not exceeding the deactivation temperature of the enzyme(s).

In the above method, it goes without saying that drying of the coated substrate is effected at a temperature below that at which there is any substantial deactivation of the enzyme, and preferably at room temperature.

In an alternative method according to the invention, the electrode may be formed by first depositing the finely divided platinum group metal or oxide optionally preadsorbed onto or admixed with finely divided carbon or graphite, with or without all or some of the binder, if used, on the surface of the electrically conductive substrate in a similar manner, i.e. by coating with a liquid suspension comprising finely divided platinum group metal or oxide optionally preadsorbed onto or admixed with finely divided carbon or graphite particles, in a suspension medium, preferably an aqueous medium, and then drying. Thereafter the dried layer is impregnated with a second solution comprising the enzyme, and optionally the, or additional, binder, thereby to disperse the enzyme into the deposited finely divided platinum or platinum oxide containing, or other platinum group metal or oxide containing layer, followed by redrying of the final product.

Instead of using the platinum group metal in finely divided elemental form, the corresponding oxides may be used such as platinum or palladium oxide. Thus all references herein to a platinised or palladised material are to be taken as including a corresponding oxide containing material unless the context requires otherwise.

Even more surprisingly, in accordance with another aspect of the present invention, and as already indicated, it has been found that, not only can the fluorocarbon resin binder be dispensed with or replaced by a low temperature, preferably water-soluble or water-dispersible, binder, the finely divided carbon or graphite can be dispensed with as well. Thus, enzyme electrodes can now be prepared consisting quite simply of an admixture of enzyme, or mixture of enzymes, and a finely divided platinum group metal, or corresponding metal oxide, deposited, with or without the aid of a binder, onto the surface of an electrically conductive carbon paper, or onto an electrically conductive carbon track. Subject to compatibility with the enzyme, other electrically conductive substrates may be used. In contact with enzyme substrate at a fixed over-potential, such electrodes show good amperometric response with a current output that is directly proportional to substrate concentration over a wide concentration range. Such enzyme electrodes, and others herein described, are therefore useful as biosensors in a wide range of applications, particularly in the field of medical and veterinary diagnostics for the measurement of enzyme substrate concentrations, e.g. glucose, lactate, cholesterol concentrations, in a wide range of medical and clinical samples.

In accordance with the method aspects of this invention, a variety of other printing or coating techniques besides screen printing may be used in applying the admixture of enzyme, finely divided platinum group metal or oxide, optionally adsorbed onto the surface of finely divided particles of carbon or graphite, and optionally containing an additional binder, to the surface of the electrically conductive support. Besides traditional coating techniques, e.g. by doctor blade or roller coating, the enzyme and finely divided platinum group metal or oxide containing mixtures may be printed onto the surface of the support by such known printing techniques as ink plotting or tampo printing.

In yet another method according to the invention, the enzyme electrodes may be prepared by initially depositing, e.g. by screen printing, onto the surface of an electrically conductive support a thin film of finely divided particles of a platinum group metal or metal oxide, optionally adsorbed onto the surface of finely divided carbon or graphite, and optionally in admixture with a low temperature binder, a binder capable of binding the particles into a coherent layer on the surface of the support without fusing or sintering of the binder, and subsequently impregnating that deposited layer with the enzyme or mixture of enzymes.

Whilst the preferred finely divided carbon and graphite materials used in accordance with the preferred aspects of this invention are finely divided activated carbon and graphite particles having finely divided particles of an elemental platinum group metal, e.g. platinum, palladium, iridium or rhodium, and preferably platinum or rhodium, adsorbed on the surface of the carbon particles, or in admixture therewith, the corresponding oxides, e.g. platinum oxide, palladium oxide and rhodium oxide, may be used instead. Hence the terms "platinised" and "palladised" as used herein are intended to include the oxides, unless the context requires otherwise. Also herein the terms "activated" carbon and "activated" graphite refer to highly porous, high surface area carbon and graphite materials obtained, for example, by heat treatment of carbon or graphite powder in steam or $CO_2$ to give a high surface area product generally referred to in the art as "activated carbon". The surface area of such activated materials may range from 10 $m^3/g$ upwards, and typically will be in the range 200 to 600 $m^3/g$. Particle size is not critical, but carbon or graphite powders having a particle size in the range 3 to 150 nm are preferred, more preferably 3 to 50 nm.

The amount of platinum group metal or oxide adsorbed onto the carbon powder will generally be sufficient to provide platinum group metal loadings in the range 0.1 to 20% by weight, based on the weight of carbon, preferably from 0.5 to 5%. These limits are, however, practical rather than critical; below about 0.1% the output signal falls to a level which in practical terms is too low to be measured, except by extra-sensitive measuring equipment. Above about 20%, the loading of platinum group metal becomes uneconomic, with little additional benefit in terms of increased response or sensitivity. Preferably the platinum group metal or oxide particles have a particle size in the range 1 nm to 20 $\mu$m and most preferably are of a colloidal size in the range 1 to 4 nm.

Where a binder is used in the enzyme electrodes of this invention, any suitable low temperature (i.e. capable of binding the platinised or palladised carbon or graphite powder/enzyme mixture at room temperature without heating to fuse the binder) binder may be used. Preferred are water-soluble or water-dispersible materials, and especially hydroxyethyl cellulose or gelatin, but other suitable binders include water-soluble and water-dispersible starch and cellulosic derivatives, e.g. starch acetate, cellulose acetate, cellulose acetate butyrate, and ethylcellulose, and other water-soluble synthetic and semi-synthetic polymers, e.g. polyvinylalcohol, polyvinyl pyrrolidone. Amounts of binder used may range from 5 to 100% on a dry weight basis, based on the combined weight of enzyme and platinised or palladised carbon powder, preferably from 20 to 50%.

Whilst the enzyme electrodes described herein may be classed as mediatorless, an electron transfer mediator such as ferrocene can be incorporated, if desired, into the suspension used to form the electrode.

Whilst the mixture of platinised or palladised carbon powder and enzyme is preferably suspended in water prior to the application thereof to the electrically conductive substrate, e.g. by screen printing, other suitable liquids including organic solvents, e.g. cyclohexanone or dichloromethane, may be used as the suspension medium. When deposited on the electrically conductive substrate, coating thickness may range from 5 to 500 $\mu$m.

Enzyme loadings will vary widely depending upon the particular enzyme or enzyme mixture used. In the case of glucose oxidase, loadings of from 10 to 5000 $\mu g/cm^2$ of electrode surface have been found satisfactory, with 100 to 2000 $\mu g/cm^2$ preferred.

As the electrically conductive substrate, a variety of different material may be used, for example, a platinum or other electrically conductive metal strip, electrically conductive synthetic polymer film, but most preferably there is used as the substrate an electrically conductive carbon paper or carbon track, i.e. a line of carbon particles deposited on a non-conductive support, such as are commercially available in the art.

Usually, but not necessarily, the surface of the enzyme electrode will be physically protected by the application of a suitably porous, e.g. polycarbonate, membrane or screen which must, of course, be permeable by the enzyme substrate (glucose) which is to be determined. Such membranes are somewhat disadvantageous in increasing the response time of the sensor, but nevertheless even with such a membrane the present sensors are capable of response times comparable with, and in many cases, substantially better than, conventional enzyme electrodes.

As already indicated, the invention relates particularly to glucose oxidase electrodes, i.e. in which the immobilised enzyme is a glucose oxidase, but it will be apparent that other oxidoreductases can be used, although not always with equivalent effect. This is not necessarily due to any inherent ineffectiveness of the enzyme, but to other factors. For example, in the determination of uric acid using uricase, the uric acid substrate itself undergoes electrochemical oxidation at the base electrode, thus largely masking any effect from the enzyme. However, other suitable oxidoreductases include lactate oxidase, galactose oxidase, cholesterol oxidase and other peroxide producing enzymes as well as combinations of immobilised enzymes, including combinations of a non-oxidase and an oxidase, the first acting on a substrate of interest to produce an oxidisable substrate for the oxidase, the latter acting on the oxidisable product to produce a measurable current which is proportional to the concentration of the substrate of interest. One such combination is the combination of beta-galactosidase and glucose oxidase (for the quantitative determination of lactose), or the combination of a beta-glucan depolymerising enzyme, beta-glucosidase and glucose oxidase (for the determination of beta-glucans).

Other types of sensor application include the use of enzymic or non-enzymic reagents or processes which interact with a primary substrate of interest in a precursor reaction, the resulting product including a substance which in turn acts as a substrate for an enzyme electrode according to this invention. Many examples of such precursor steps will be found in the field of immunochemical reactions, and methods of using such reactions in the construction of sensors utilizing enzyme electrodes according to the present invention will be apparent to those skilled in the art.

However, the primary application of the electrodes according to the invention will be as biosensors for the detection and/or quantitative measurement of an oxidisable substrate, especially glucose, in a sample, especially a clinical sample such as blood, serum, plasma, urine, sweat, tears and saliva.

Other possible, non-clinical applications include:
(a) fermentation monitoring,
(b) industrial process control,
(c) environmental monitoring, e.g. effluent and pollution control of liquids and gases,
(d) food testing,
(e) veterinary applications, particularly applications allied to the clinical applications suggested above.

In so far as bio- and other sensors incorporating an enzyme electrode material according to the present invention may comprise other structural elements, electrical leads, electrically non-conductive (insulating) supports or probes, etc., such elements in the construction are conventional and need not be described in detail. Electrical contact with the electrode material may be made in many ways, for example, by mounting the electrode material in face to face contact with an electrically conductive contact or terminal, e.g. of platinum or other suitable conductor.

In use, the current output of the enzyme electrodes of this invention, in the presence of a sample containing enzyme substrate, will be measured at a fixed potential in accordance with procedures already well established in the art. Generally speaking, current outputs will be measured at a fixed potential in the range 200 to 600 mV with reference to a silver/silver chloride reference electrode. Two examples of suitable two and three electrode cells for use in making such measurements are illustrated and described in detail in International Patent Publication No. WO 87/07295 to which reference has already been made.

The invention is illustrated by the following Examples and in which reference is made to the accompanying drawings in which FIGS. 1 to 17 illustrate the current output from various enzyme electrodes constructed in accordance with this invention.

EXAMPLE 1

A glucose oxidase electrode was prepared by suspending 200 mg of platinised carbon powder containing approximately 10% by weight of platinum, and obtainable from The Prototech Company, Newton Highlands, Mass. (Vulcan XC-72 carbon powder, nominal particle size 30 nm having colloidal platinum, particle size range 1.5 to 2.5 nm adsorbed thereon) in 400 µl phosphate buffer ($NaH_2PO_4$, 2 mmol/L; $Na_2HPO_4$, 16 mmol/L; NaCl, 100 mmol/L; $K_2H_2(EDTA)2H_2O$, 1 mmol/L; pH 7.4). To the suspension were then added 40 mg glucose oxidase. The suspension was stirred and allowed to stand for one hour at room temperature.

After standing the suspension was spread by hand as a thin film on the surface of a sheet of electrically conductive carbon paper (Toray backing paper) and left to dry at room temperature.

Figure 16:
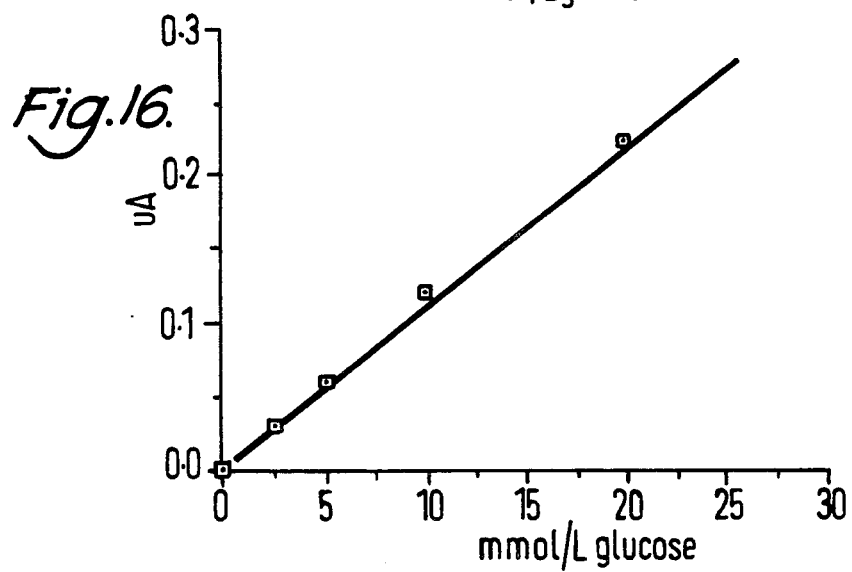
FIG. 16 shows the current output (uA) from the electrode of Example 14 to various concentrations of glucose, when using cellulose acetate butyrate in dichloremethane as the binder.

When dry the enzyme electrode material was cut into 1.5 mm discs and tested for its response to glucose at 400 mV vs. Ag/AgCl in a two electrochemical cell as described in WO 87/07295 with reference to FIG. 16.

The current output (µA) from the electrode to various concentrations of glucose is shown in FIG. 1 of the accompanying drawings. The results obtained show two remarkable effects, firstly that the electrode response is substantially linear over the whole range of from 0 to 30 mmoles/L glucose, and secondly that those results are obtained without any binder to provide an "oxygen rich" atmosphere. According to the prior art, WO 87/07295 excepted, it has previously been possible to obtain linearity only over a limited range of glucose concentrations, e.g., 2 to 5 mmol/L (Yao T., Analytica Chimica Acta 148, 27-33 (1983)). Further prior art teaches that the linearity of the response of glucose electrodes increases when free diffusion of oxygen is permitted (Lobel E. and Rishpon J., Analytical Chemistry 53, 51-53 (1981)) which teaching is supported in WO 87/07295 where a binder is used having a high affinity or solubility to oxygen. In contrast, the present invention provides linearity of a response over a much wider range of glucose concentrations, even when no binder is present.

EXAMPLE 2

Example 1 was repeated but using finely divided platinised graphite (5% Pt) obtained from Johnson Matthey Chemicals, Royston, United Kingdom, and supplied by them as a "process catalyst" CH15959/01, in place of the platinised Vulcan XC-72. An essentially similar linear electrode response is obtained, see FIG. 2.

EXAMPLE 3

Example 2 was repeated, i.e. using the finely divided platinised graphite (5% Pt) obtained from Johnson Matthey to form the enzyme/Pt graphite suspension. In this case, however, a 20% w/v solution of gelatin in water cooled to 37° C. was added to the suspension at a volume ratio of 2:1.

Figure 3:
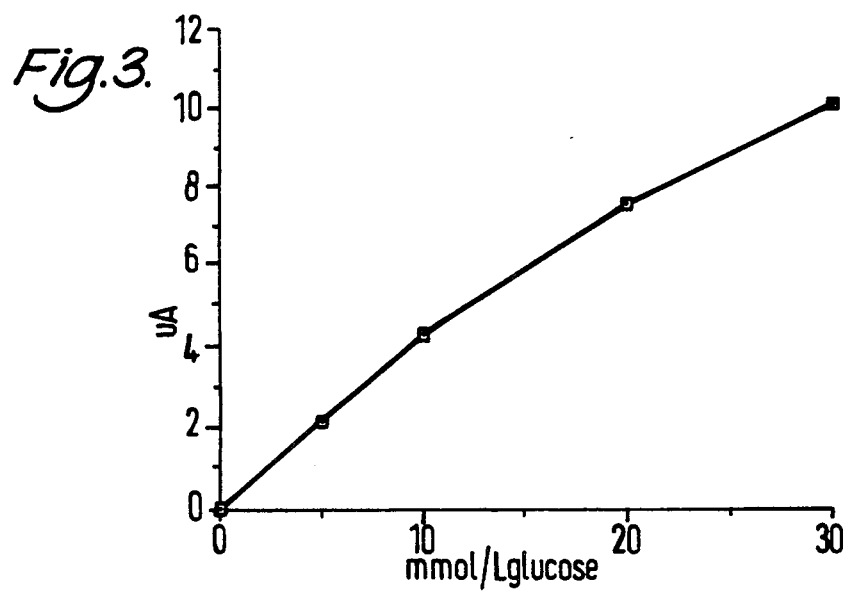
FIG. 3 shows the current output (uA) from the electrode of Example 3 to various concentrations of glucose[of Example 3].

The resultant electrode, obtained by spreading the gelatin-containing paste onto the Toray backing paper gave, after drying at room temperature, a more robust product but again showing a substantially linear response to glucose, see FIG. 3.

EXAMPLE 4

An aqueous paste was prepared from 45 mg platinised carbon powder (Vulcan XC-72, containing 10% by weight adsorbed colloidal platinum; The Prototech Company, Massachusetts), 5 mg glucose oxidase suspended in 100 mg of a 10% solution of hydroxyethyl cellulose in 0.1M KCl. The paste was coated by hand on prewetted carbon paper (Toray backing paper) and allowed to dry.

1.5 mm discs were cut from the dried electrode material and tested for their response to glucose in a 2-electrode cell as described and at a potential of 400 mV versus Ag/AgCl.

Figure 4:
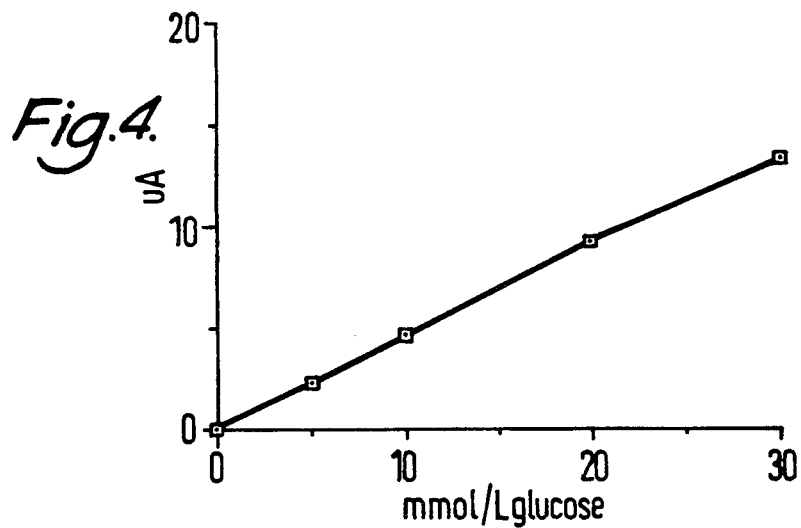
FIG. 4 shows the current output (uA) from the electrode of Example 4 to various concentrations of glucose[of Example 4].

The current output was measured at various glucose concentrations, and the results are presented in FIG. 4. The response is essentially linear over a glucose concentration range of from 0 to 30 mmol/L.

EXAMPLES 5 AND 6

Figure 5:
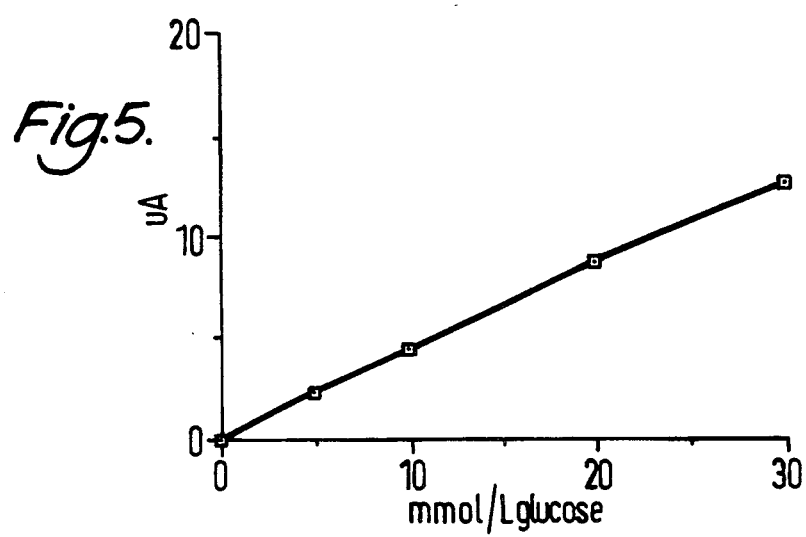
FIG. 5 shows the current output (uA) from the electrode of Example 5 using 1% platinum in the platinised carbon powder to various concentrations of glucose[of Example 5, when using 1% platinum of the platinised carbon powder].
Figure 6:
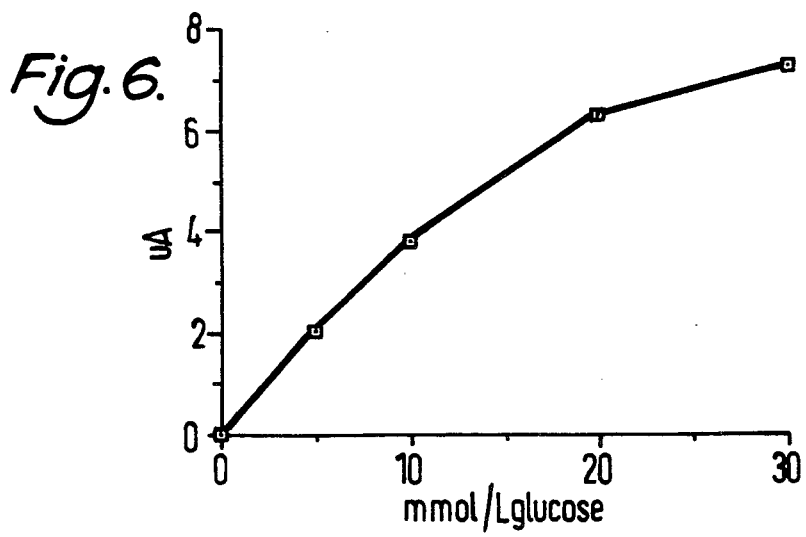
FIG. 6 shows the current output (uA) from the electrode of Example 6 using 0.2% platinum in the platinised carbon powder to various concentrations of glucose[of Example 6 when using 0.2% platinum in the platinised carbon powder].

The procedure of Example 4 was repeated, but with platinised carbon powder (Vulcan XC-72) containing 1% and 0.2% platinum respectively. Current outputs of the electrode materials were measured under the same conditions and the results are presented in FIGS. 5 and 6. FIG. 5 shows a similar linear response to glucose concentrations over the whole range of 0 to 30 mmol/L. The reduced amount of platinum (0.2%) shows a substantial degree of linearity, but over a reduced concentration range of 0 to 20 mmol/L.

EXAMPLE 7

Figure 7:
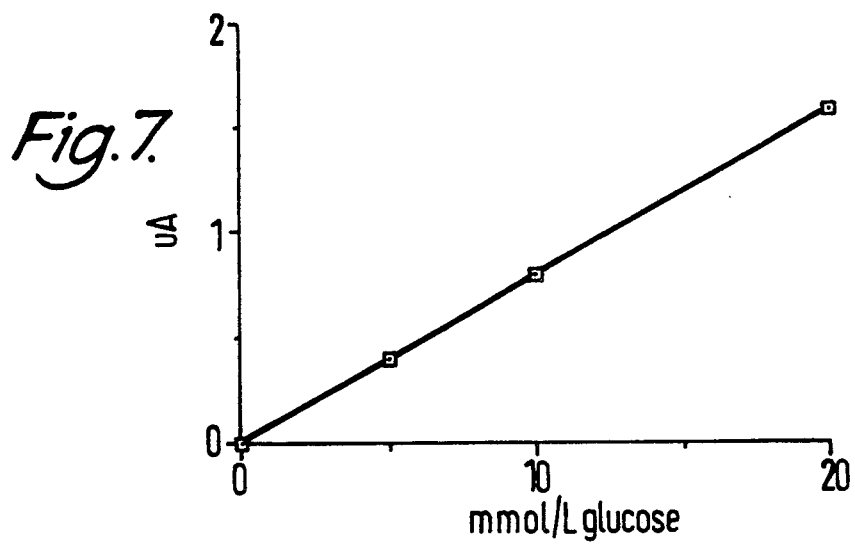
FIG. 7 shows the current output (uA) from the electrode of Example 7 using 0.5 mg of glucose oxidase to various concentrations of glucose[of Example 7 when using 0.5 mg of glucose oxidase].

Example 4 was repeated but using 0.5 mg of glucose oxidase. The current output from the electrode material measured under the same conditions is shown in FIG. 7. Linearity is obtained over glucose concentrations of from 0 to 20 mmol/L.

EXAMPLE 8

Example 4 was repeated but using 45 mg of carbon powder (Vulcan XC-72) containing 10% by weight colloidal platinum oxide adsorbed thereon in place of platinum metal.

Figure 8:
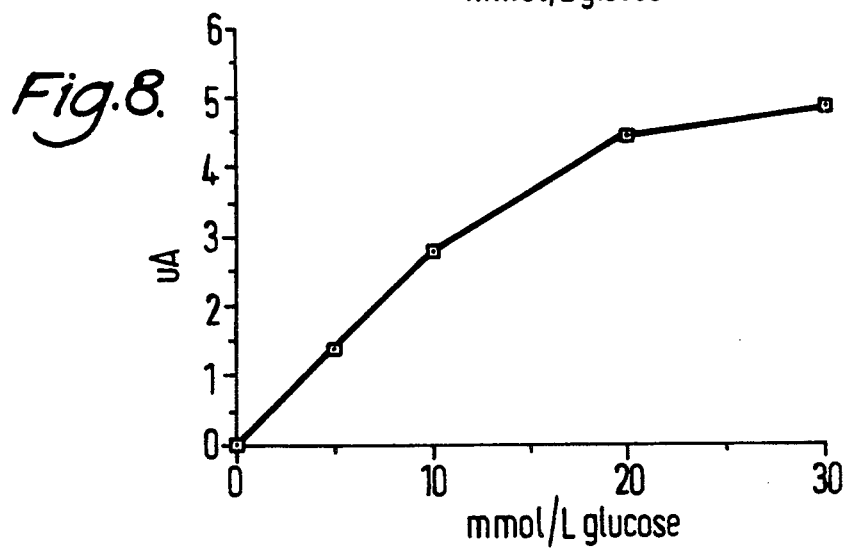
FIG. 8 shows the current output (uA) from the electrode of Example 8 using 45 mg of carbon powder containing 10% by weight colloidal platinum oxide to various concentrations of glucose[of Example 8 when using 45 mg of carbon powder containing 10% by weight colloidal platinum oxide].

1.5 mm discs of the electrode material were tested for their response to various glucose concentrations under the same conditions as before, i.e. in a 2-electrode cell at a potential of 400 mV versus Ag/AgCl. The current output measured at various glucose concentrations is shown in FIG. 8.

EXAMPLE 9

A paste was prepared by mixing 5 mg platinum black, 400 mg activated carbon powder (Vulcan XC-72), 5 mg glucose oxidase in 100 mg hydroxyethyl cellulose (10%) in 0.1M KCl.

The paste was smeared by hand onto Toray backing paper and allowed to dry.

1.5 mm discs were cut from the dried electrode material and tested for their response to glucose under the same conditions as before.

Figure 9:
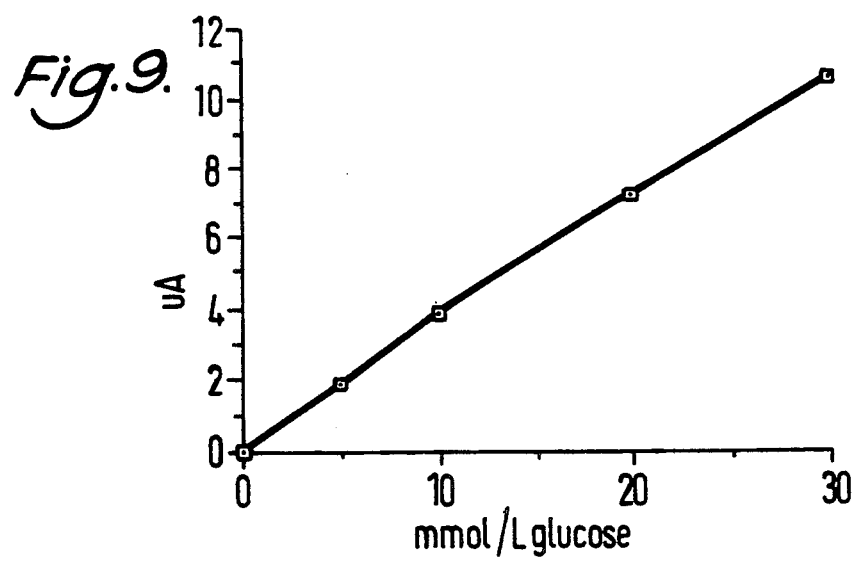
FIG. 9 shows the current output (uA) from the electrode of Example 9 prepared using 5 mg platinum glack, 400 mg carbon powder, 5 mg glucose oxidase, and 100 mg hydroxyethyl cellulose (10%) in 1.M KCl as the binder to various concentrations of glucose[of Example 9 when using 5 mg platinum black, 400 mg carbon powder, 5 mg glucose oxides in 100 mg hydroxyethyl cellulose (10%) in 1.M KCl].

The electrode shows a linear response to glucose over the whole concentration range of 0 to 30 mmol/L as shown in FIG. 9.

EXAMPLE 10

Example 4 was repeated but using 5 mg lactate oxidase EC 1.1.3.2 in place of the glucose oxidase.

1.5 mm discs of the dried electrode material were tested for their response to lactate under the same conditions as previously: 2-electrode cell at 40 mV versus Ag/AgCl.

Figure 10:
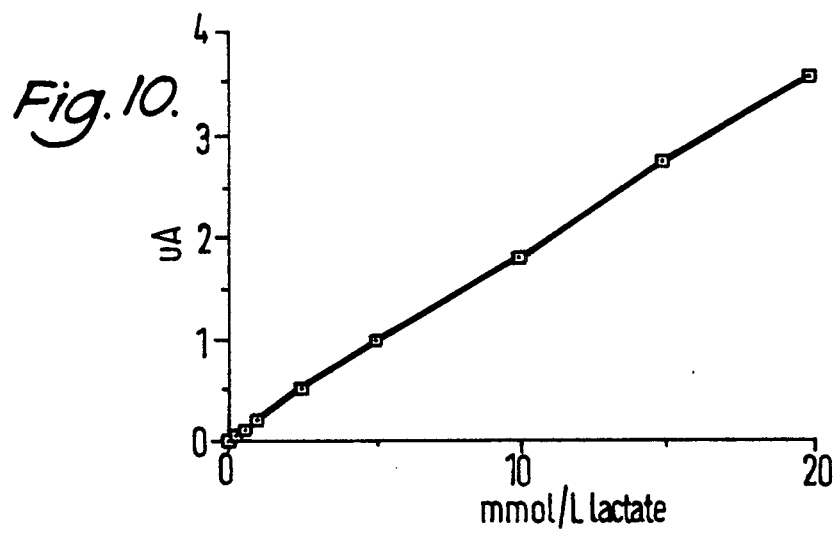
FIG. 10 shows the current output (uA) from the electrode of Example 10 prepared using 5 mg of lactate oxidase in place of glucose oxidase to various concentrations of lactate [glucose of Example 10 when using 5 mg of lactate oxidase in 100 mg of glucose oxidase].

As shown in FIG. 10, the current output varies substantially linearly with lactate concentration over lactate concentrations ranging from 0 to 20 mmol/L.

EXAMPLE 11

A carbon-less enzyme electrode was prepared by suspending 5 mg platinum black, 5 mg glucose oxidase in 100 mg of 10% hydroxyethyl cellulose in 0.1 M KCl.

The suspension was smeared by hand onto Toray backing paper and dried.

Figure 11:
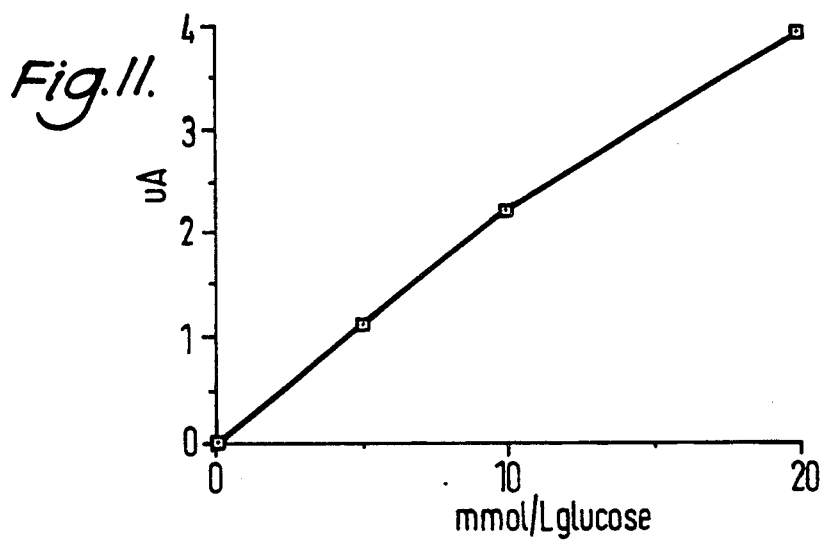
FIG. 11 shows the current output (uA) from the electrode of Example 11 prepared using 5 mg platinum black, 5 mg glucose oxidase, and 100 mg of 10% hydroxyethyl cellulose in 0.1M KCl as the binder to various concentrations of glucose[of Example 11 when using 5 mg platinum black, and 5 mg glucose oxidase in 100 mg of 10% hydroxyethyl cellulose in 0.1M KCl].

1.5 mm discs of the dried electrode material were tested as before for electrode response, current output, to various glucose concentrations. The results are shown in FIG. 11, and show a substantially linear response over glucose concentrations in the range 0 to 20 mmol/L.

EXAMPLE 12

Figure 12:
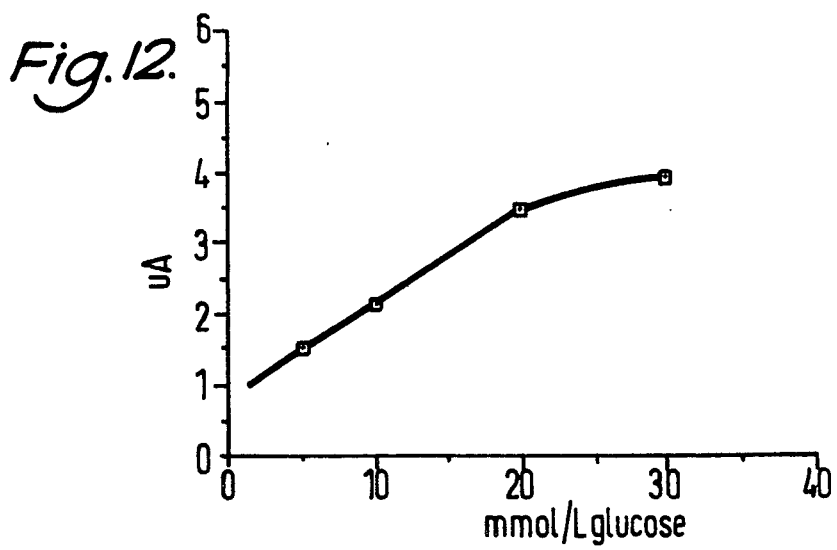
FIG. 12 shows the current output (uA) from the electrode of Example 12 prepared using activated carbon particles having adsorbed thereon 1% by weight, finely-divided colloidal particles of iridium in place of platinised carbon power and using a phosphate buffer in place of 0.1M KCl in the binder to various concentrations of glucose[of Example 12 when using activated carbon particles having adsorbed thereon 1% by weight, finely divided colloidal particles of Iridium in place of platinised carbon powder and using a phosphate buffer in place of 0.1M KCl].
Figure 13:
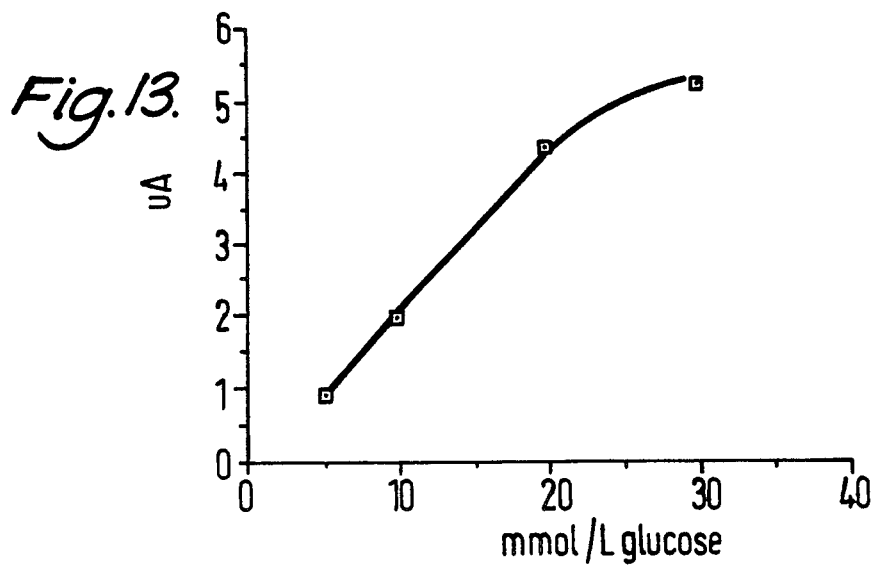
FIG. 13 shows the current output (uA) from the electrode of Example 12 prepared using activated carbon particles having adsorbed thereon 1% by weight, finely-divided colloidal particles of rhodium in place of platinised carbon powder and using a phosphate buffer in place of 0.1M KCl in the binder to various concentrations of glucose[of Example 12 when using activated carbon particles having adsorbed thereon 1% by weight, finely divided colloidal particles of Rhodium in place of platinised carbon powder and using a phosphate buffer in place of 0.1M KCl].

Following the same general procedure as Example 4, but using activated carbon particles (Vulcan XC-72) having adsorbed thereon 1% by weight (based on the weight of the carbon) of, respectively, finely divided colloidal particles of iridium and rhodium, in place of the platinised carbon powder, and using a phosphate buffer (see Example 1 for details of the suspension medium) in place of 0.1 M KCl, glucose oxidase electrodes were prepared consisting of a homogeneous layer of rhodium or iridium-containing graphite particles and glucose oxidase bonded with hydroxyethylcellulose onto a carbon paper backing layer. The response in microamps of such electrode material cut into 1.5 mm discs to substrate (glucose) concentrations in the range 0 to 40 mmol/L at 400 mV versus an Ag/AgCl reference electrode is shown in FIGS. 12 and 13 respectively (FIG. 12, iridium; FIG. 13 rhodium). Again a substantially linear response is obtained. The high level of response obtained with rhodium is particularly to be noted.

EXAMPLE 13

8 mg cholesterol oxidase ($\sim$16 $\mu$/mg) was mixed with 150 $\mu$l of 5% w/v hydroxyethylcellulose solution in a phosphate buffer ($NaH_2PO_4$ 1.6 mmol/L; $Na_2HPO_4$ 5.3 mmol/L; NaCl 52 mmol/L; EDTA 0.15 mmol/L; pH 7.4) until dissolved. 72 mg of finely divided platinised graphite (5% Pt) were added and mixed to form a paste.

Electrically conductive carbon paper (Toray) soaked for two weeks in a phosphate buffer ($NaH_2PO_4$ 2 mmol/L; $Na_2HPO_4$ 16 mmol/L; NaCl 100 mmol/L; EDTA 1 mmol/L; Triton X100 surfactant 0.1% v/v; pH 7.4) was blotted dry and the cholesterol oxidase/platinised graphite/HEC paste spread evenly thereon by hand. The resulting paste electrode was dried at room temperature for 2 hours and at 30° C. for 30 minutes. To improve shelf life, the electrode was then dipped in 5% w/v sucrose solution for 2 minutes and dried at 20° C. for 1 hour.

When dry the paste electrode was cut into 1.5 mm discs and tested for response to cholesterol in a two-electrode cell at a potential of +340 mV versus Ag/AgCl, the paste electrode being protected by a 0.05$\mu$ polycarbonate (Nucleopore) membrane. For testing, standard cholesterol solutions were prepared from 6 mM cholesterol stock solution in 22% water soluble $\beta$-cyclodextrin (Molecusol) in phosphate buffer (phosphate 1 mmol/L; NaCl 100 mmol/L; EDTA 1 mmol/L, pH 7.4) at dilution rates to give standard concentrations 0.5,1,2,4 and 6 mmol/L.

Figure 14:
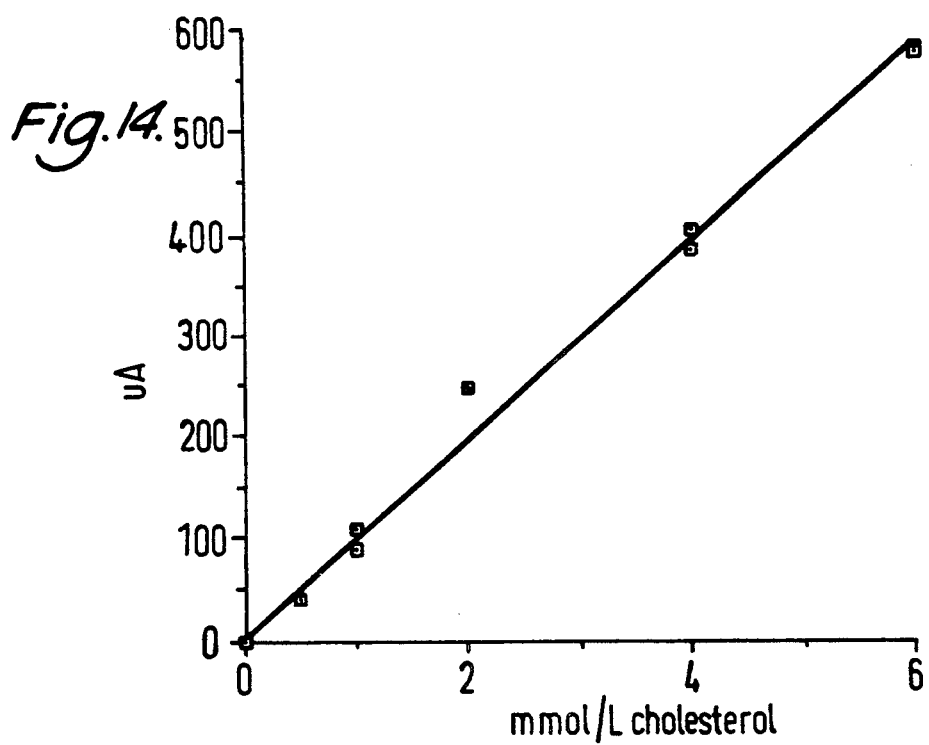
FIG. 14 shows the current output (uA) from the electrode of Example 13 to various concentrations of cholesterol in the range of 0 to 6 mmol/L.

The current output in $\mu$A is shown in FIG. 14, and shows an essential linear response to cholesterol concentrations in the range 0 to 6 mmol/L.

EXAMPLE 14

Enzyme electrodes according to the invention were prepared using non-aqueous systems as follows.

Paste suspensions were prepared using 10 mg quantities of glucose oxidase and 40 mg quantities of platinised graphite powder (5% Pt) in non-aqueous binder systems as follows:

(a) 400 $\mu$l 10% w/v cellulose acetate in cyclohexanone;
(b) 600 $\mu$l 5% w/v cellulose acetate butyrate in dichloromethane;
(c) 400 $\mu$l 5% w/v ethylcellulose in cyclohexanone.

Following mixing, the pastes were spread onto electrically conductive carbon (Toray) backing paper and left to dry at room temperature.

Figure 15:
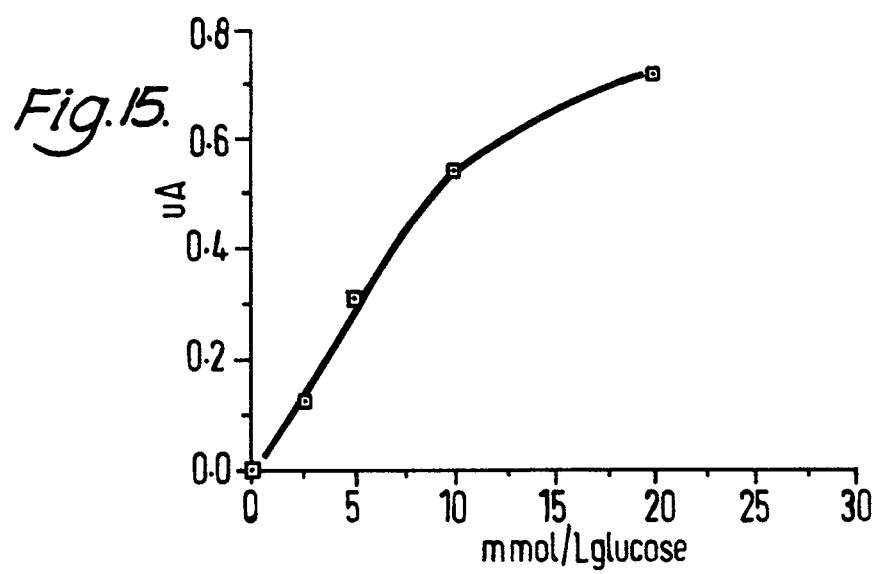
FIG. 15 shows the current output (uA) from the electrode of Example 14 to various concentrations of glucose, when using cellulose acetate in cylohexanone as the binder.
Figure 17:
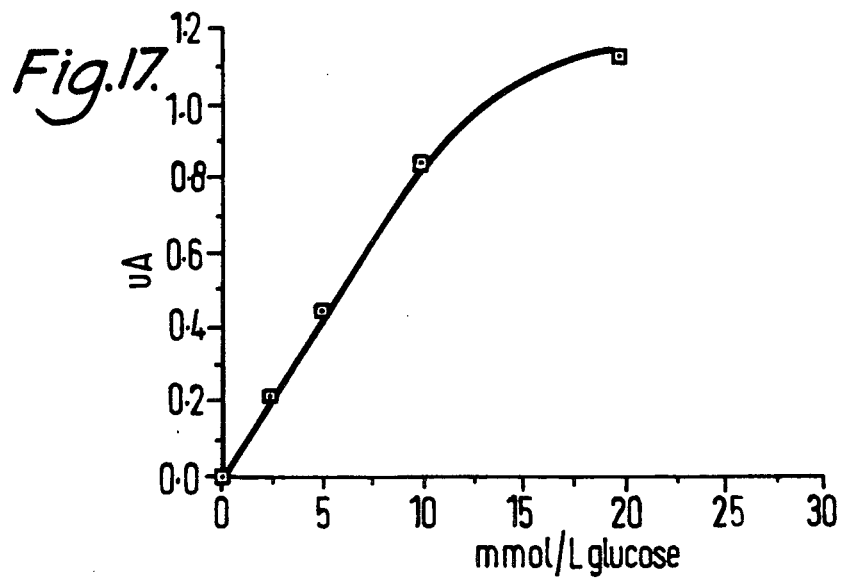
FIG. 17 shows the current output (uA) from the electrode of Example 14 to various concentrations of glucose, when using ethylcellulose in cyclohexanone as the binder.

When dry, 1.5 mm diameter discs were cut from the coated backing paper and tested for their response to glucose in a two-electrode cell at 340 mV versus Ag/AgCl. The electrode material was mounted on a gold working electrode and held in position thereon by a 0.03$\mu$ polycarbonate (Nuclepore) membrane. Standard glucose solutions were used containing 0, 2.5,5,10 and 20 mmol/L glucose in a phosphate buffer containing $NaH_2PO_4$ 2 mmol/L; $Na_2HPO_4$ 16 mmol/L; NaCl 100 mmol/L; EDTA 1 mmol/L; and pH 7.4. In each case the current output in $\mu A$ from the cell is illustrated graphically in FIGS. 15 to 17 as follows:

FIG. 15 cellulose acetate in cyclohexanone;

FIG. 16 cellulose acetate butyrate in dichloromethane;

FIG. 17 ethylcellulose in cyclohexanone.

These Figures demonstrate the feasability of performing the invention using non-aqueous systems and alternative low temperature binders.

I claim:

1. A method for the manufacture of enzyme electrodes comprising a substantially homogeneous mixture of a finely divided platinum group metal or oxide and one or more enzymes deposited as an electrically conductive layer upon the surface of an underlying support, the electrode being amperometrically responsive to the activity of the enzyme when the enzyme containing a layer of the electrode is in contact with the respective enzyme substrate, the method comprising forming a substantially uniform suspension comprising the finely divided platinum group metal or oxide and said enzyme(s) suspended in a liquid suspension medium, depositing that suspension on the surface of the support member, and drying the deposited suspension at a temperature below the deactivation temperature of the enzyme thereby to deposit the finely divided platinum group metal or oxide and said enzyme(s) as a substantially uniform, homogeneous coating layer on the surface of the support.

2. A method according to claim 1, wherein the suspension also contains a low temperature binder, said low temperature binder being effective to bind the finely divided platinum group metal or oxide and enzyme together to form a cohesive layer on the surface of the support at a temperature not exceeding the deactivation temperature of the enzyme(s), said layer comprising a substantially homogeneous dispersion of said finely divided platinum group metal or oxide and said enzyme.

3. A method according to claim 2, wherein the suspension also contains particles of finely divided carbon or graphite.

4. A method according to claim 3, wherein the particles of finely-divided platinum group metal or oxide are preadsorbed onto the surface of the finely divided carbon or graphite particles.

5. A method according to claim 4, wherein finely divided carbon or graphite particles have a particle size in the range 3 to 150 nm, and wherein the finely divided platinum group metal or oxide preadsorbed thereon has a particle size in the range 1 to 4 nm.

6. A method according to claim 1, wherein the liquid suspension medium is an aqueous medium.

7. A method according to claim 2, wherein the binder is gelatin or hydroxyethylcellulose.

8. A method according to claim 1, wherein the suspension is applied to the surface of the support member by a printing process.

9. A method according to claim 8, wherein the suspension is applied to the support member by screen printing.

10. A method according to claim 1, wherein the support member is itself electrically conductive.

11. A method according to claim 10, wherein the electrically conductive substrate is an electrically conductive carbon paper or carbon track.

12. A method according to claim 1, wherein the finely divided platinum group metal component is finely divided platinum or rhodium.

13. A method according to claim 1, wherein the enzyme used is glucose oxidase, lactate oxidase, or cholesterol oxidase.

14. In a method for the manufacture of enzyme electrodes comprising a substantially homogeneous mixture of a finely-divided platinum group metal or oxide adsorbed onto the surface of particles of a finely divided carbon or graphite powder and one or more enzymes deposited as a surface layer on the surface of an underlying electrically conductive support, the electrode being amperometrically responsive to the activity of the enzyme when the electrode is in contact with the respective enzyme substrate, the improvement which comprises forming an initial suspension comprising the enzyme, the finely divided carbon or graphite having said platinum group metal preadsorbed thereon, a binder operable to bind the enzyme and the platinum group metal or oxide containing carbon or graphite into a substantially uniform homogeneous layer on the surface of the support at a temperature below that at which the enzyme is deactivated, suspended in a liquid carrier, depositing the suspension as a uniform layer on the surface of the support, and drying the deposited layer at a temperature below the deactivation temperature of the binder.

15. A method according to claim 14, wherein the suspension is deposited on the surface of the support by printing.

16. A method according to claim 14, wherein the suspension is deposited on the surface of the support by screen printing.

17. A method according to claim 14, wherein the liquid carrier for the suspension is aqueous.

18. A method according to claim 17, wherein the binder is hydroxyethylcellulose or gelatin.

19. A method according to claim 14, wherein the electrically conductive support comprises an electrically conductive carbon paper.

20. A method according to claim 14, wherein the finely divided carbon or graphite comprises as said platinum group metal, finely divided platinum or rhodium.

21. A method according to claim 14, wherein the enzyme is glucose oxidase, lactate oxidase or cholesterol oxidase.

22. In a method for the manufacture of enzyme electrodes comprising a substantially homogeneous mixture of a finely-divided platinum group metal or oxide adsorbed onto the surface of particles of a finely divided carbon or graphite powder and one or more enzymes deposited as a surface layer on the surface of an underlying electrically conductive support, the electrode being amperometrically responsive to the activity of the enzyme when the electrode is in contact with the respective enzyme substrate, the improvement which comprises depositing as a surface layer on the surface of the electrically conductive support a suspension comprising the finely divided platinum group metal or oxide preadsorbed onto the surface of a finely divided graphite powder and a low temperature binder operable to bind the finely divided carbon or graphite powder and said enzyme into a uniform substantially homogeneous layer on the surface of the support at a temperature below the deactivation temperature of the enzyme, suspended in a liquid carrier, drying the deposited layer of platinum group metal or oxide containing carbon or graphite particles and said binder, impregnating the deposited layer with a suspension of the enzyme in a liquid carrier, and redrying the impregnated enzyme containing surface layer at a temperature below the deactivation temperature of the enzyme.

23. A method according to claim 22, wherein the carrier liquids for the platinised graphite or carbon suspension and the enzyme are both aqueous.

24. A method according to claim 23, wherein the binder is hydroxyethylcellulose or gelatin.

25. A method according to claim 22, wherein the support is an electrically conductive carbon paper.

26. A method according to claim 22, wherein the platinised carbon or graphite suspension is deposited on the support by screen printing.

27. An enzyme electrode comprising a substantially homogeneous mixture of a finely divided platinum group metal or oxide and one or more enzymes deposited as an electrically conductive surface layer on the surface of an underlying support member, said layer also containing a binder for the particles of finely divided platinum group metal or oxide and said enzyme(s), wherein said binder comprises a material effective to bind the finely divided platinum group metal or oxide particles and said enzyme(s) into a coherent, cohesive layer bonded to the support at a temperature not exceeding the deactivation temperature of the enzyme(s).

28. An enzyme electrode according to claim 27, wherein the binder is water-soluble or water-dispersible.

29. An enzyme electrode according to claim 28, wherein the binder is gelatin or hydroxyethylcellulose.

30. An enzyme electrode according to claim 27, wherein the enzyme containing layer also contains particles of finely divided carbon or graphite.

31. An enzyme electrode according to claim 30, wherein said finely divided particles of platinum group metal or oxide are preadsorbed onto the surface of the carbon or graphite particles.

32. An enzyme electrode according to claim 31, wherein the carbon or graphite particles have a particle size in the range 3 to 150 nm and the preadsorbed platinum group metal or oxide particles have a size in the range 1 to 4 nm.

33. An enzyme electrode according to claim 27, wherein the enzyme containing layer is printed onto the surface of the underlying support member.

34. An enzyme electrode according to claim 30, wherein the enzyme containing layer is screen printed onto the surface of the support member.

35. An enzyme electrode according to claim 27, wherein the underlying support member is itself electrically conductive.

36. An enzyme electrode according to claim 35, wherein the support member comprises a sheet of electrically conductive carbon paper or carbon track.

37. An enzyme electrode according to claim 27, wherein the enzyme containing layer contains as the platinum group metal component finely divided platinum or rhodium.

38. An enzyme electrode according to claim 27, wherein the enzyme containing layer contains a said enzyme glucose oxidase, lactate oxidase or cholesterol oxidase.

39. An enzyme electrode comprising a substantially homogeneous mixture containing the enzyme and a finely divided platinum group metal or oxide preadsorbed onto the surface of a finely divided carbon or graphite deposited on the surface of an electrically conductive support and containing a low temperature binder effective to bind the enzyme and finely divided platinum group metal or oxide containing particles into a uniform cohesive layer on the surface of the support at a temperature below the deactivation temperature of the enzyme.

40. An enzyme electrode according to claim 39, wherein the binder is water-soluble or water dispersible.

41. An enzyme electrode according to claim 40, wherein the binder is gelatin or hydroxyethylcellulose.

42. An enzyme electrode according to claim 39, wherein the electrically conductive support comprises an electrically conductive carbon paper or carbon track.

43. An enzyme electrode according to claim 39, wherein the layer of enzyme, platinised graphite or carbon and binder, is screen printed on the surface of the support.

44. An enzyme electrode according to claim 39, wherein the finely divided platinum group metal preadsorbed onto the surface of the finely divided graphite or carbon is platinum or rhodium.

45. An enzyme electrode according to claim 39, wherein the enzyme is glucose oxidase, lactate oxidase or cholesterol oxidase.

* * * * *